United States Patent [19]

Conn et al.

[11] Patent Number: 4,553,965
[45] Date of Patent: Nov. 19, 1985

[54] FLUID-EXPANSIBLE CONTRACEPTIVE TAMPON AND APPLICATOR

[76] Inventors: Shepard Conn, 27 Washington Pl., Metuchen, N.J. 08840; Arnold Kushner, 110-27 Jewel Ave., Forest Hills, Queens, N.Y. 11375

[21] Appl. No.: 626,607

[22] Filed: Jul. 6, 1984

Related U.S. Application Data

[60] Continuation of Ser. No. 516,665, Jul. 25, 1983, abandoned, which is a continuation of Ser. No. 208,011, Nov. 18, 1980, abandoned, which is a division of Ser. No. 906,984, May 17, 1978, Pat. No. 4,271,835.

[51] Int. Cl.⁴ .................................................. A61F 13/20
[52] U.S. Cl. .................................... 604/286; 604/55; 604/904
[58] Field of Search .................. 604/904, 15, 55, 285, 604/286, 385

[56] References Cited

U.S. PATENT DOCUMENTS

| | | | |
|---|---|---|---|
| 1,601,707 | 9/1926 | Oepping | |
| 2,391,343 | 12/1945 | Popper | 128/127 |
| 2,467,884 | 4/1949 | Elias | 128/270 |
| 2,832,342 | 4/1958 | Wingenroth | 128/263 |
| 3,054,403 | 9/1962 | Baker | 128/270 |
| 3,056,997 | 10/1962 | Cummings | 15/511 |
| 3,335,726 | 8/1967 | Maranto | 128/270 |
| 3,512,528 | 5/1970 | Whitehead et al. | 128/285 |
| 3,521,637 | 7/1970 | Waterbury | 128/270 |
| 3,559,646 | 2/1971 | Mullan | 128/270 |
| 3,643,661 | 2/1972 | Crockford | 128/263 |
| 3,696,812 | 10/1972 | Jaycox | 128/263 |
| 3,780,730 | 12/1973 | Weisman | 128/127 |
| 3,918,452 | 11/1975 | Cornfeld | 128/270 |
| 3,994,298 | 11/1976 | Des Marais | 128/285 |
| 4,010,751 | 3/1977 | Ring | 128/263 |
| 4,271,835 | 6/1981 | Conn et al. | 128/270 |
| 4,274,410 | 6/1981 | Chvapil | 128/270 |

FOREIGN PATENT DOCUMENTS

2024930 12/1971 Fed. Rep. of Germany .

OTHER PUBLICATIONS

"Historical Perspectives on Intravaginal Contraceptive Sponges" by Kenneth K. Keown, Jr., M.A. Division of Surgical Biology, Department of Surgery Health Sciences Center, University of Arizona, Tucson, Ariz. 85712, Contraception 1977.
"Laboratory and Clinical Testing of an Intravaginal Contraceptive Collagen Sponge" by Milos Chvapil et al., Contraception, Jun. 1977, vol. 15, No. 6.
"An Intravaginal Contraceptive Diaphragm Made of Collagen Sponge: New Old Principle" by Milos Chvapil, Fertility and Sterility, vol. 27, No. 12, Dec. 1976.
"The Acceptance of the Collagen Sponge Diaphragm as an Intravaginal Contraceptive in Human Volunteers" by Milos Chvapil et al., Fertility and Sterility, vol. 27, No. 12, Dec. 1976.

Primary Examiner—C. Fred Rosenbaum
Assistant Examiner—S. Vinyard
Attorney, Agent, or Firm—Lane & Aitken

[57] ABSTRACT

A method and apparatus for contraception wherein an applicator houses a fluid-expansible, hydrophilic, tampon material in its unactivated, compressed state separate from a reservoir of spermicide or medicament. The applicator preferably includes a manually frangible portion of the spermicide reservoir or a fluid communication passage to bring the spermicide into contact with the fluid-expansible tampon material upon command prior to use. After activating by moistening, the spermicide-impregnated, expanded tampon can be readily inserted into a vagina by use of the applicator. Preferably, the tampon is made from a body of purposefully-compressed, memory-retentive, hydrophilic material having a resilience and a high coefficient of expansion when moistened to act as a barrier to the os uteri, to fill the vaginal fornices and absorb ejaculate. Various shapes of the tampon are disclosed, as are methods of making and using the invention.

7 Claims, 19 Drawing Figures

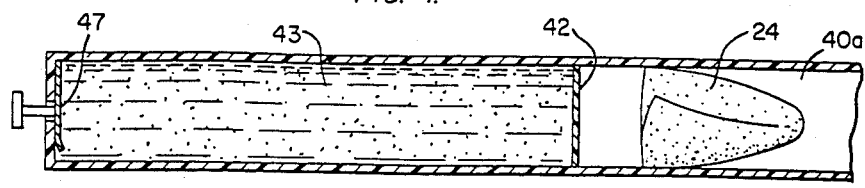
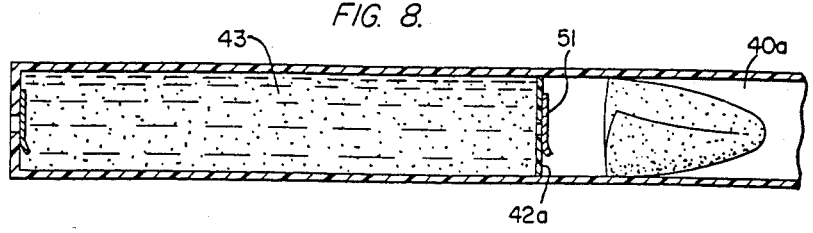
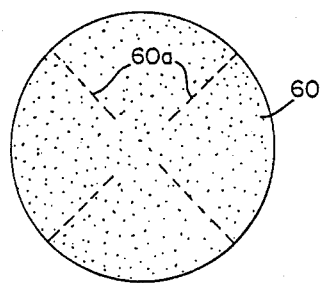
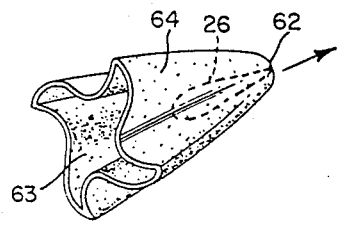
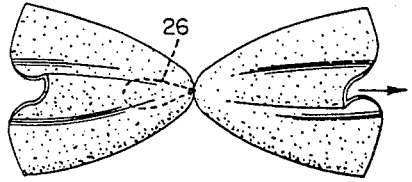
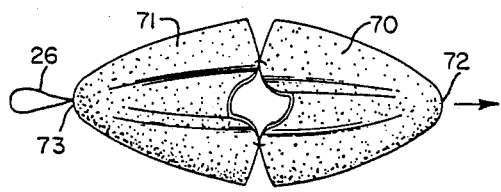

FLUID-EXPANSIBLE CONTRACEPTIVE TAMPON AND APPLICATOR

This application is a continuation of application Ser. No. 516,665, filed July 25, 1983 now abandoned, which in turn is a continuation of application Ser. No. 208,011, filed Nov. 18, 1980 now abandoned, which is a divisional of application Ser. No. 906,984, filed May 17, 1978, now U.S. Pat. No. 4,271,835.

BACKGROUND OF THE INVENTION

This invention relates to a method and apparatus for contraception. More particularly, this invention relates to an applicator which houses, preferably, a hydrophilic, fluid-expansible material in a quiescent, compressed, unactivated state in a first chamber separate from a second chamber which acts as a reservoir for a spermicide or medicament. The applicator includes means for bringing the spermicide into contact with the tampon upon command prior to use, as well as means for delivering the spermicide-moistened tampon to a vagina and positioning it therein. Still more particularly, this invention relates to a combination of an applicator of the type described with a tampon made from a body of purposefully-compressed, memory-retentive, hydrophilic, fluid-expansible material with a high coefficient of expansion and which is resilient when moistened or activated prior to insertion into a vagina. Still more particularly, this invention relates to a method of making and using the apparatus and the tampon according to the invention, as well as to various shapes for the contraceptive tampon.

Mankind has long sought an effective method and apparatus for contraception for purposes of population control, for family planning, and to prevent unwanted pregnancies. While a number of contraceptive techniques have been proposed, many of which have been clinically effective, each has suffered from various types of shortcomings for a number of reasons. For example, the use of oral contraceptives has been found to be associated with a number of adverse side effects, some of which are fatal. Also, intrauterine devices have been known to cause lesions, and even to perforate the uterus. Further, IUD's are spontaneously rejected from the uterus in a significant number of women.

The so-called barrier type of contraception has long been included among such contraceptive proposals. Many barrier contraceptives are efficient and benign. However, they often require special motivation for their use by reason of the fact that they may, especially if rigid or semi-rigid, in the first place have to be fitted precisely by a physician. Even more importantly, in actual use, they are unesthetic and therefore unacceptable to many women. Further, many barrier contraceptives require application just prior to coitus and may be said to be coitally-related, a factor which discourages their use.

By way of background, the human vagina may be considered a closed-end collapsed cylinder. The uterine cervix, which varies from 1 to 4 cm in length, protrudes into the closed end. The uterine cervix may point directly into the axis of the cylinder, or backward (which is the most common orientation) or forward. The potential spaces around the cervix are called fornices and include an anterior, a left, a right, and a posterior fornix. A contraceptive barrier, to be effective, must be in contact with the cervix to block the os uteri, and ideally should fill all of the fornices to prevent the inadvertent migration of semen into the cervical mucus.

An intravaginal anticonception tampon was referred to in the *Papyros Ebers*, circa 1550 B.C., and has been in use in one form or another for more than 3500 years. However, there have been no reliable scientific reports of its efficacy. Such tampons have included sponges moistened with fluid having spermicidal qualities. At least as early as the time of the ancient Egyptians, a tampon of lint impregnated with drugs and honey was said to be capable of contraceptive qualities when placed in the vagina of the user. Later, but at least as early as the nineteenth century, a suitable soft sponge tied by a ribbon and properly placed high in the vagina, was said to possess contraceptive qualities. Thus, historically, it is known that a suitable sponge properly placed in contact with all vaginal fornices and well moistened with an effective spermicidal solution should act as an effective contraceptive by virtue of (1) its barrier action, (2) its absorption and retention of ejaculate, and (3) prolonged spermicidal action.

It has remained a problem of convenience and esthetics for the user of a resilient barrier-type contraceptive to prepare and insert it into a vagina prior to intercourse. In addition to actual or perceived non-esthetic qualities of such a preparatory act, such preparations may be inconvenient, susceptible to miscalculation such as by insufficient or excess moistening with spermicide, the premature or tardy application of spermicide, and the like. Accordingly, it is an overall object of this invention to provide a suitable contraceptive tampon of barrier design and function made from absorbent material which can be impregnated with a precisely metered amount of spermicide in an applicator and conveniently inserted into the vagina by using the applicator in such a way that the moistened tampon material acts as an effective contraceptive. The applicator, after having served to moisten the tampon and to insert it into the vagina, is disposed of. The tampon is intended to remain in place, once positioned in the vagina, for as long as 24 hours, during which time coitus may take place one or more times. Thereafter, it is removed and disposed of by the user.

While the prior art has focused its attention on compressible sponge-like members, such as made from sea sponges, or viscose and cellulose materials whose shape in the quiescent state is approximately the same as its shape in the active implanted state, it is another purpose of this invention to utilize a compressed (without having to be physically restricted to enforce compression), dry tampon material which, immediately prior to vaginal insertion can be moistened with an effective spermicidal solution. When moistened, the compressed material expands markedly either prior to introduction into the vagina or when placed in the vagina. By using such an expansible material, the contraceptive tampon, in the dry, unactivated state, can be stored in a small, handy compartment in an applicator, and can expand to a clinically effective size after moistening to serve as a barrier to os uteri and, at the same time, also fill the fornices.

In order to improve convenience and the esthetic character of the contraceptive act, it is a significant aspect of this invention to provide an applicator for the expansible hydrophilic tampon retained in a chamber separate from a reservoir for spermicidal solution. Upon command, it is the aim of this invention to bring the spermicide into contact with the tampon to expand it to its active size and shape and to use the applicator as an insertion device for the tampon into its intended position.

It is another object of this invention to provide a disposable, compact applicator-tampon system which can be conveniently used to wet the tampon with a spermicide stored in the applicator and insert it into the vagina with a minimum of manipulations and moving parts.

It is a further object of this invention to provide a new use as a barrier contraceptive for a purposefully-compressed, memory-retentive, hydrophilic material which in its unactivated state is compact, but which becomes resilient and absorbent as it expands to a clinically effective size and shape upon moistening with a spermicide or medicament.

These and other objects of the invention will become apparent from the foregoing description of the embodiment taken in conjunction with the accompanying drawings.

BRIEF SUMMARY OF THE INVENTION

Directed to achieving the aforestated objects and overcoming the problems in connection with prior art barrier-type contraceptive devices, the invention, in one aspect, relates to a compact, disposable applicator which comprises at least a pair of telescoping, cylindrical members made from a pliant plastic material. One of the cylindrical members acts as a reservoir for a precisely metered amount of spermicide or medicament and is thus closed. That member includes a closed end adjacent to a tampon stored in its dry unactivated state in a chamber defined by the other cylindrical member. The end opposite the closed end of the first cylinder defines a vent and filler opening to permit the first cylinder to be filled and the vent to be sealed by a removable tab. Preferably, the closed end of the first cylinder contains a plurality of score lines or is otherwise readily frangible by the application of pressure by the user to release at least a small amount of spermicide from the spermicide reservoir to the fluid-expansible tampon.

Upon contact with the small amount of released spermicide, the adjacent portion of the fluid-expansible tampon expands within the second cylinder. Thereafter, the tab is removed to release the remaining spermicide to wet and expand the entire tampon to its desired degree. After moistening within the second cylinder by the spermicide, the first cylinder is caused to telescope within the second cylinder within the vagina to insert the spermicidally effective tampon into position high in the vagina. Release from the applicator permits the tampon to expand further and act as a clinically effective barrier to the os uteri, to fill the fornices, and to further act as an absorbent for ejaculate, particularly in cases of repeated intercourse.

It is a second feature of this invention to provide a new use as a barrier contraceptive to a compressed, memory-retentive, hydrophilic, fluid-expansible material, which can be stored in an unactivated state in a compact manner and yet become resilient and expand into a desired size and shape for insertion and upon insertion into the vagina of the user. Such materials are well known in other arts and have a high degree of expansibility when wetted. For purposes of this specification, the "quiescent state" of the tampon refers to its unactivated, compressed state prior to impregnation with a spermicide or medicament, and prior to insertion into the body of the user. Similarly, the "dry" state of the compressed hydrophilic material, for example, one made of cellulose, refers to the state of the material prior to impregnation with a spermicide or medicament, while including a normal moisture level inherent in such material or in the normal environment for the material within the applicator. Such materials are memory-retentive. That is, the materials can be purposefully heated to expel moisture and compressed to a desired compact size which compresses and collapses the cellular structure of the material. Such materials thus retain the collapsed or compressed state in the absence of the application of moisture and without requiring physical restrictions or retraints to retain the compressed state. Such materials are commercially available. Examples of suitable materials are known in the trade as "Supercel" and "Normandy" and are available from the American Sponge & Chamois Co. of Long Island City, N.Y., among others.

It is a further object of this invention to provide a plurality of shapes for the tampon of the type described, including a cylindrical or oval disc, folded into a shape resembling a folded umbrella to be inserted into the vagina. A second such member can be joined either apex-to-apex or at a plurality of points along the circumference of the disc or at the centers of each disc in order to form two-layer barrier-type devices. In another configuration, the tampon material in quiescent state is folded in such a manner as to be inserted edgewise into the vagina after activation by moistening. In still another embodiment, a plurality of particulate segments of the tampon material are contained within a porous fluidpermeable membrane to be wetted in the manner described to expand into an approximately cylindrical or spherical configuration. Other shapes for the tampon are also disclosed.

These and other features of the invention are described hereinafter in the detailed description of the invention taken in conjunction with the drawings.

BRIEF DESCRIPTION OF THE DRAWINGS

In the drawings:

FIG. 7 is a side cross-sectional view of an alternative embodiment of the applicator according to the invention;

FIG. 8 is a side cross-sectional view of still another alternative embodiment of the applicator according to the invention;

FIGS. 9 and 9A show a disc of tampon material and a folded umbrella shape for the body of the tampon;

FIG. 10 shows a pair of folded umbrella body shapes connected together so that their apexes are axially pointed in opposite directions;

FIG. 11 shows a pair of folded umbrella body shapes connected together at their peripheries;

DETAILED DESCRIPTION OF THE PREFERRED EMBODIMENTS

Figure 1:
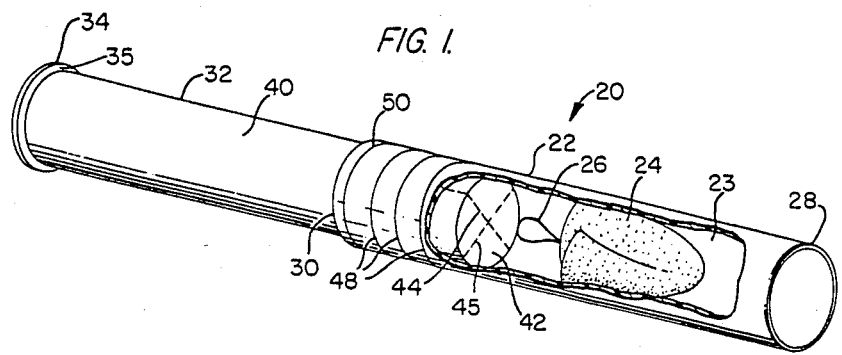
FIG. 1 is a perspective view of the manually-frangible applicator according to the invention, partially cut away to show a compressed tampon in its quiescent state.

In FIG. 1, a perspective of the applicator according to the invention, designated generally by the reference numeral 20, is shown in a partially cutaway perspective view. The applicator 20 includes a first member 22 defining an open-ended chamber 23 for receiving a folded compressed tampon 24 which upon wetting acts as a contraceptive tampon as will be discussed in greater detail later in this specification. The tampon 24 has a string or cord 26 secured thereto to remove the tampon from the vagina when appropriate to dispose thereof. If desired the chamber 23 may be closed by a removable cover member secured to the member 22.

The member 22 is preferably made from a flexible thin-wall plastic material defining an opening at the outer distal end 28 thereof. The outer end 28 is preferably rounded and the exterior wall of the member 22 is preferably smooth to avoid irritation of the tissues of the vagina when the member 22 containing the tampon 24 is inserted therein to expel the tampon for contraception.

The inner end 30 of the outer telescoping member 22 is structurally adapted to receive a second member 32 in a telescoping relationship wherein the inner wall of the member 22 comfortably mates with the outer wall of the member 32 to permit free ingress and egress of the member 32 into the interior member 22.

Figure 2:
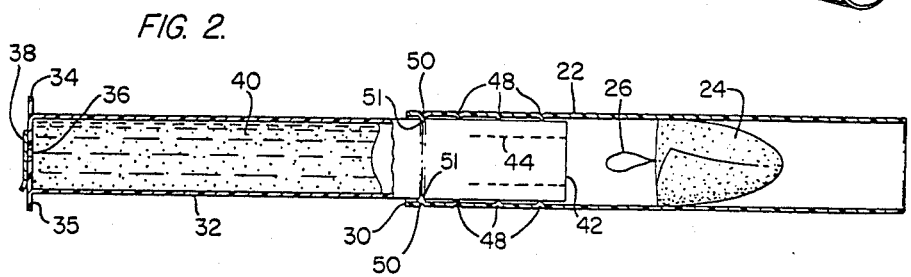
FIG. 2 is a side cross-sectional view of the embodiment of FIG. 1.

As best seen in FIG. 2, the inner end of the member 32 includes an upraised flange portion 34, the inner edge 35 of which will abut the edge 30 of the member 22 when the member 32 is completely extended into the interior of the member 22. The flange portion 34 also provides a convenient gripping surface for the hand of the user during utilization of the device.

As best seen in FIG. 2, the outermost surface of the member 32 defines an opening 36 which serves as a filler and vent opening. The opening 36 may be covered by an adhesively secured, removable member 38, such as a plastic tab, paper liner, or the like. With the tab 38 in place, the member 32 serves as a closed reservoir for a fluid spermicide or medicament designated generally by the reference numeral 40. The fluid 40 may be introduced into the reservoir defined by the member 32 through the opening 36 which thereafter is sealed by the tab 38 to retain the fluid therein until the applicator 20 is used. A number of known effective spermicides and medicaments available in the fluid state may be used. For example, a 5% solution of the commonly-used spermicidal agent nonoxonol-9 may be used.

Figure 3:
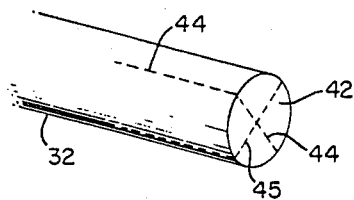
FIG. 3 is a partial end view of the spermicide-containing cylinder showing the score-lines to facilitate manual fracturing of the cylinder to release the spermicide.

The surface 42 of the member 32 includes a plurality of score lines 44 and 45 sufficient in depth to permit the fracture of the inner end of the member 32 by the application of pressure against the flexible assembly of the members 22 and 32 in the area of the score lines. As shown in FIG. 3, the score lines may extend along a portion of the length of the member 32 to permit a more complete rupture of the end of the member in use. The location and depth of the score lines are a function of the material used, its thickness, and its frangibility characteristics.

In the embodiment shown in FIG. 2, a plurality of annular rings 48 may be provided on the member 22 to provide a convenient gripping surface for the user. A raised detent ring 50 on member 22 is in register with the depressed detent ring 51 on the member 32 to retain the members in the position shown in FIG. 2. The annular rings 48 act as both finger grips on the outer surface of the member 22 and as bearing surfaces for application of pressure on the end of the member 32 to fracture it when desired. A raised detent 50 on the member 22 is in register with a corresponding depressed detent of the member 32 to fix the member 32 in the extended position shown in FIGS. 1 and 2. The dimensions of the raised detent ring 50 are such that the members 22 and 32 are retained in a position that can easily be overcome by a moderate force applied axially to the member 32.

When pressure is applied to the applicator 20 by manually gripping the end 30 of the member 22 in the area of the score lines 44 and 45 on the inner end 42 of the member 32, the inner end of the member 32 is caused to rupture to release a small amount of spermicide to begin to moisten the contraceptive tampon 24 in the position shown in FIG. 1. Subsequent removal of the tab 38 permits the ingress of air through the opening 36 to cause the remaining fluid in the reservoir defined by the member 32 to be released to the tampon to complete its wetting and moistening.

Retaining the tab 38 in position covering the opening 36 after fracture of the inner end 42 of the spermicide reservoir defined by the number 32 has a significant advantage in connection with the use of the applicator. Because a small amount of spermicide escapes the reservoir when the scored end of the member 32 is fractured, the inner end of the tampon 24 adjacent to the outer end of the member 32 is moistened. When moistened, the tampon end will expand and fill the diameter of the member 22 in the area adjacent to the fractured end of the member 32, thereby to prevent leakage of the remaining spermicide between the tampon and the interior wall of the member 22. Thereafter, when the tab 38 is removed, the remainder of the spermicide will flow to moisten the remainder of the tampon. Preferably, this action is caused to occur with the apparatus 20 located in a vertical alignment or in such alignment so that gravity assists the flow of the fluid 40 and the orientation of the applicator 20 is such as to prevent the loss of spermicide through the opening 36. Moreover, because the initial escape of spermicide had caused the top end of the tampon 24 to expand and fill the diameter of the member 22, the remainder of the fluid which flows from the reservoir defined by the member 32 is prevented from escaping between the outer surface of the tampon 24 and the inner surface of the member 22 and thus avoiding its effective utilization.

As shown in FIG. 1, the length of the member 32 from end 30 of the member 22 to the end 35 of the member 32 will be on the order of 7 cm in order to provide a comparable length between the end 42 of the member 32 and the end 28 of the member 22 for receiving the folded tampon 24. Thus, the overall dimension of the member 22 will be related to this length and to the volume necessary in the reservoir 32 as determined by the volume of fluid necessary and desirable to moisten the tampon 24. Therefore, the area of overlap of the two cylinders must be sufficient to provide a constant rigidity for maintaining the two members in juxtaposition, and sufficient space for the finger gripping as described in connection with FIG. 2. Preferably, the length of the member 22 is equal to the overall length of the member 32 so that, in use, the member 32 is completely telescoped within the member 22 for complete expulsion and proper positioning of the tampon in the vagina.

Enough fluid is provided from the reservoir defined by the member 32 to sufficiently moisten the tampon 24. In its contraceptive function, the degree of moistening by spermicide is such as to impart an expansion to the tampon while leaving the tampon with enough absorbent capacity remaining in the tampon to accommodate ejaculate during intercourse. The median ejaculate volume is about 4-8 ml within the normal range of 2 and 10 ml. If it is desired to accommodate two or three consecutive usages, the size of the tampon and the degree of moistening can be selected to receive for example, 12 to 15 ml of semen. In any event, it is desirable to retain at least some absorbent capacity for semen in the tampon to improve its effectiveness and reliability.

Figure 4:
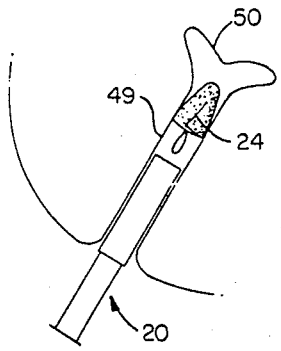
FIG. 4 is a non-detailed view showing the applicator according to the invention inserted into a vagina for expelling the impregnated tampon therefrom.

FIG. 4 is a view of the applicator 20 according to the invention after insertion into a vagina 49. The tampon 24 has been ejected from the applicator to a position high in the vagina 49 to act as a barrier to the os uteri 50. Some degree of expansion of the tampon 24 occurs after insertion both because prior to expulsion the expansion of the tampon had been confined by the physical dimensions of the member 22 and partially because of a further absorption of vaginal fluid when positioned.

Figure 5:
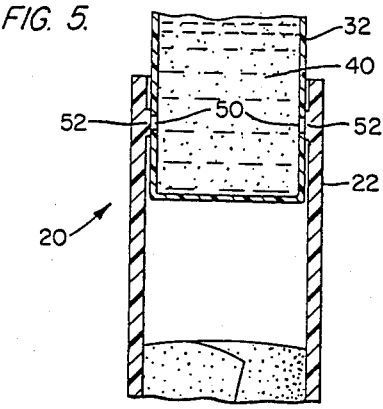
FIG. 5 is a side cross-sectional view of an alternate embodiment showing a sealed passageway in the wall of the reservoir defined by the second applicator member.
Figure 6:
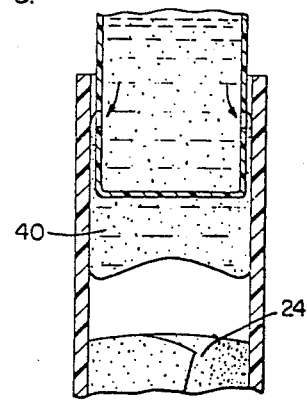
FIG. 6 is a view similar to FIG. 5 showing the passageway after unsealing by relative movement between the first member and the second member.

An alternative embodiment for the applicator of FIGS. 1-4 is shown in FIGS. 5 and 6. In FIGS. 5 and 6, like reference numerals on like parts have been used. In the position shown in FIG. 5, the wall of the member 32 contains a pair of diametrically opposed openings 50 which are sealed by virtue of their being positioned against the inwardly-directed nibs 52 located on the inner surface of the member 22 in register with the openings 50. Rotation of the member 32 disengages the opening 50 from the nibs 52 (as shown in FIG. 6) to permit the egress of a small amount of fluid 40 from the reservoir defined by the member 32 in the manner similar to that previously described. Thereafter, removal of the tab 38 and the expulsion of the tampon into the vagina may proceed as previously described.

Other more complex valving mechanisms may also be utilized to communicate by a predetermined passageway the fluid from the reservoir to the tampon location. Therefore, the embodiments of FIGS. 5 and 6 are intended to be illustrative. For example, a centrally located, axially-extending tube could extend from the member 22 toward the closed but fracturable or penetratable end of the member 32. By telescoping the members 22 and 32 slightly, the tube could be injected into the reservoir to permit the passage of spermicide to the tampon.

Alternatively, the function of the member 32 (to act as a fluid reservoir) and the function of the member 22 (to house the compressed tampon) may be combined into a single member as shown in FIG. 7, the entire structure forming a single tube made from a flexible elastomeric material with a fracturable partition 42 separating the cavity 43, which serves as a fluid reservoir, from cavity 40a, which serves as a housing for the tampon 24. In this alternative design, the partition 42, scored to facilitate fracturing, is caused to fracture by the user's application of finger pressure on the outer surface of the tube in the vicinity of the partition 42, thereby releasing a small amount of fluid to wet and, thus, expand the end of the tampon 24 adjacent to the partition 42 so that it fills the entire diameter of the tube. Upon completion of the initial, partial, moistening of the tampon, a valve flap 47 is depressed allowing an ingress of air and causing the remainder of the fluid to flow from the reservoir 43 into the cavity 40a wherein the tampon 24 is contained and so to fully moisten the tampon 24 with a precisely metered amount of fluid. Subsequent to full discharge of fluid into the tampon 24, the open end of the tube 28 is inserted into a vagina and the elastomeric tube is alternately and repeatedly pressed and released in a pumping action to propel, by means of air pressure, the tampon 24 out of the chamber 40a and into place in the vagina. A flap valve arrangement 47, located at the end of the reservoir 43 is so fashioned that alternate finger pressure on and release of the tube on the outer surface of the cavity 43 will cause a build-up of air in sufficient pressure in the chamber 43 to cause the volume of air to push against the end of the tampon 24 adjacent to the fractured partition 42 and, in so doing, cause the tampon 24 to be expelled from the open end of the tube into the vagina.

In still another alternate design, the fracturable partition 42 is supplanted by a partition 42a with an opening covered by a flap valve 51 as depicted in FIG. 8. In this case, the outer surface of the tube can be pumped by finger pressure in the vicinity of the chamber 43 to expel fluid into the cavity 40a and, when all the fluid is exhausted, the air that replaces it through the valve entrance 48 will eventually force the moistened, expanded tampon from the end of the tube and into the vagina.

The tampon 24 according to the invention may be provided in a number of shapes to achieve its intended purpose as a barrier-type contraceptive device capable of easy insertion into the vagina by use of the applicator 20 and readily removable therefrom by means of a retrieval loop 26, while effectively acting as a contraceptive. While a number of materials may be used, such as ordinary compressible sponges, viscose, cellulose, collagen sponges, polyurethane, vinyl sponges, rubber sponges and other fluid absorbent materials, the material most suitable for utilization in a compact applicator is shown as a compressed, fluid-expansible, hydrophilic cellulose material having a memory capability when compressed to its quiescent state. In this respect, the material is similar to a commercially available expansible cellular material. Specific examples of suitable materials are known in the trade as "Supercel" and "Normandy" and are available from the American Sponge & Chamois Co. of Long Island City, N.Y., among others. The material is characterized in that it has a high coefficient of expansion from its dry or quiescent state to its moistened state on the order of 5-20 times the original volume or more, may be purposely dried under compression to occupy a significantly small volume and thereafter expand upon moistening.

FIGS. 9 and 9A illustrate one shape of the tampon for use according to the invention. A compressed, dry, cellulose, hydrophilic disc is designated generally by the reference numeral 60. The disc 60 is preferably cut from a sheet of such material and scored along the lines 60a to facilitate folding into the shape shown in FIG. 9A. The disc 60 is approximately 6 cm in diameter and is approximately 1 mm thick. In certain designs, the disc 60 may have a plurality of notches cut into the perimeter.

The removal loop 26 is then stitched to a point at the center of the disc 60. Thereafter, the disc of FIG. 9 is folded along the score lines 60a and twisted tightly on a mandrel to provide a shape shown in FIG. 9A. After folding, the folded disc 60a is inserted, while tightly folded, into the applicator as previously described. The folded disc may be oriented in either direction along its axis so that, in one configuration, the apex 62 is inserted first into the vagina while in another, the apex is inserted last.

A single disc of the type described will unfold from its umbrella-like shape to take a position in the vagina adjacent the os uteri. This configuration will seat comfortably in most individuals in such a way that the center 62 of the face of the disc lies adjacent the os uteri while the folds 64 thereof will expand to fill the fornices. Moreover, during intercourse, the head of the penis will tend to push the tampon contraceptive well into place rather than slide between the outer folds of the tampon and the adjacent vaginal wall. This occurs principally because of the tendency of the tampon to expand outwardly to occupy the greatest circumferential area, as well as because the trailing end 63 presents a receptacle for receiving the penis. Another advantage of the single disc design of FIG. 9 is that it points inwardly in place toward the os uteri and is thus easily inserted. The trailing edges 63 will tend to preserve an orientation toward the entrance to the vagina and, thus, resist expulsion from the vaginal tract. Moreover, the loop 26 is not uncomfortable to the male and is readily available to extract the tampon. Preferably, it is removed several hours after intercourse to permit its spermicide capabilities to act as well as to absorb as much semen as possible after ejaculation.

FIG. 10 is composed of a pair of members folded as described in connection with FIGS. 9 and 9A. The pair of members 70 and 71 are sewn together at their peripheries with an anatomically acceptable thread (e.g. cotton, polyester, nylon, surgical thread, or the like) to form a pair of umbrellas having oppositely facing rounded frontal end portions 72 and 73 respectively.

FIG. 11 shows still another configuration in which a double disc assembly is joined apex-to-apex and enfolded in umbrella-like fashion with circumferential portions facing in opposite directions. In this design, the trailing edge of the rearmost member has the advantages of the member of FIG. 9A for resisting expulsion from the vagina. Further, by virtue of the firm fastening of the center of the foremost disc to that of the rearmost disc, upon expansion of the double-disc assembly, tension will be created in such a fashion that the centers of each disc will form concavities. The benefits of such concavities are as follows: The concavity of the foremost disc will tend to "cap" the uterine entrance and the concavity of the rearmost disc will tend to form a natural mode of receiving the head of the penis whereby said penis will be enabled to push the entire double-disc assembly more firmly into the upper reaches of the vagina and thus to seal more effectively against the migration of semen into the os uteri and the fornices.

Figure 12:
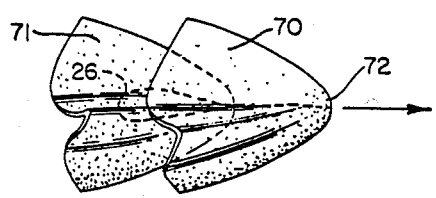
FIG. 12 shows a pair of folded umbrella body shapes connected together so that the apexes are axially pointed in the same direction.

In another configuration, the members may have their rounded closed end coaxially pointing in the same direction, as shown in FIG. 12. In this embodiment the trailing edge of the rearmost member has the advantages of the member of FIG. 9A for resisting expulsion and being pushed higher in the vagina by the penis. Moreover, the ease of insertion is retained since the rounded, closed ends of both members 70 and 71 face in the same direction toward the os uteri and both members 70 and 71 resist expulsion from the vagina.

Figure 13:
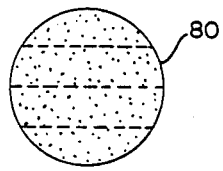
FIG. 13 shows a disc of tampon material with folds indicated for edgewise insertion into the applicator and therefore into a vagina.
Figure 14:
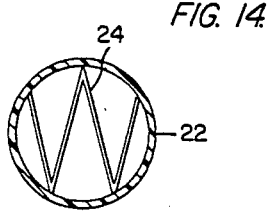
FIG. 14 shows an end view of the disc of FIG. 13 folded therein.
Figure 15A:
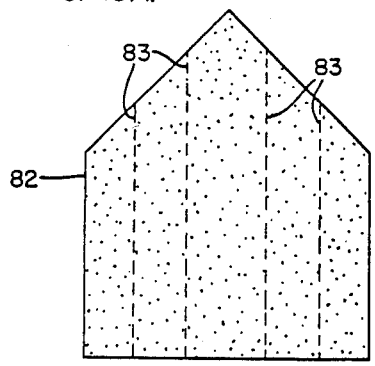
FIGS. 15A–15C show alternative blank shapes for the tampon body for folding edgewise as in the case of the embodiment of FIG. 13.
Figure 15B:
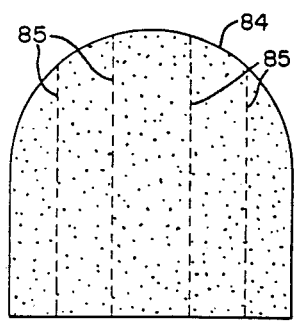
Figure 15C:
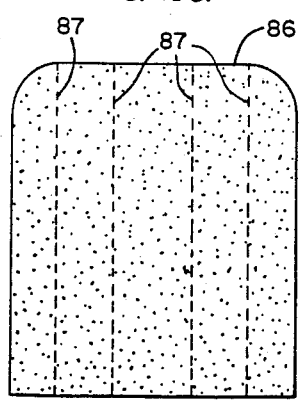

FIG. 13 shows an alternate way for folding a disc 80 of the type shown in FIG. 9 in the configuration, resembling the letter "W" in cross section. An end view of the applicator 20 shown in FIG. 14 depicts the disc in its folded state and inserted into the tube 22. This embodiment differs principally from the axially-insertable embodiments of FIGS. 9-12 in that it is inserted edgewise into the vaginal tract after expulsion from the applicator. The disc 80 enters the upper vault of the vagina laterally and is pushed by the plunger member 32 of the applicator to cover the os uteri. In using this embodiment, the loaded applicator must be oriented properly by the user so that the plane of the disc after expansion acts as a barrier. An advantage of this embodiment, however, resides in the fact that the material need not be formed as a disc. Rather, shapes such as those representatively shown by the reference numerals 82, 84, 86 in FIGS. 15A through 15C can also be used, after folding along the fold lines 83, 85, and 87 respectively. The relative ratios of the folds and the number of folds are selected within an overall width of about 6 cm and a length of about 7 or 8 cm. The embodiment of FIG. 15A is in the shape of an irregular pentagon, that of FIG. 15B in the shape of a squared circle, while that of FIG. 15C is a rectangle with rounded corners.

Figure 16:
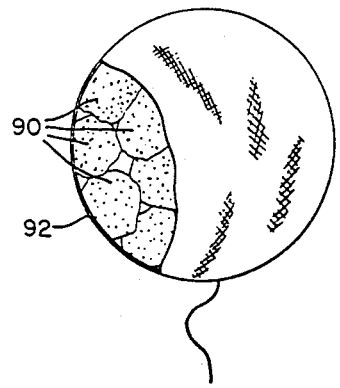
FIG. 16 shows a plurality of particulated tampon bodies of the type described with a porous casing for expansion into a generally spherical configuration.

FIG. 16 is an alternate embodiment in which a plurality of randomly-positioned particulated tampons 90 of the type described are positioned and enclosed in a porous enclosure 92. Upon wetting, the overall configuration is generally spherical for insertion in the vagina in the manner described.

As an alternative embodiment of this invention, the cylindrical member as seen in FIG. 2 which acts as a reservoir for a spermicide or medicament is sealed after having been filled through the filler hole 36 with said spermicide or medicament under pressure from a compressed gas, such as air, carbon dioxide, vinyl chloride, fluorocarbon or the like, most especially, however, gases of a nature that will not react chemically with the spermicide or medicament or will not, in any manner, be harmful to human tissue. Such gas, under pressure, will provide potential energy to act as propellant to the spermicide or medicament sealed with it in the reservoir member. With the applicator held in a vertical position so that the compressed gas is above the level of fluid spermicide or medicament, upon fracturing of or opening the valve at the end of said member that is adjacent to the fluid-expansible tampon stored in the second cylindrical member, the gas will force the entire amount of fluid to flow toward the expansible tampon and thus to wet said tampon.

The invention may be embodied in other specific forms without departing from its spirit or essential characteristics. The present embodiments are, therefore, to be considered in all respects as illustrative and not restrictive, the scope of the invention being indicated by the claims rather than by the foregoing description and all changes which come within the meaning and range of the equivalents of the claims are therefore intended to be embraced therein.

What is claimed is:

1. As a new use for a known material, the method of using a body of purposefully compressed, compression self-retentive, hydrophilic, fluid expansible material having a high coefficient of expansion and the capability of becoming resilient upon wetting as a barrier contraceptive by wetting said body with a spermicide and inserting said body intravaginally to act as a barrier to the os uteri and to fill the fornices of the upper vault of the vagina, including the steps of storing said body in a container adjacent the stored body of said spermicide and releasing said spermicide upon command to moisten said body prior to intravaginal insertion, wherein the body is shaped during compression from two discs of said material into a pair of folded umbrella configurations each having its apex pointed in the same direction, and joining said two discs; and inserting said compressed folded umbrella configuration into said container.

2. As a new use for a known material, the method of using a body of purposefully compressed compression self-retentive, hydrophilic, fluid expansible material having a high coefficient of expansion and the capability of becoming resilient upon wetting as a barrier contraceptive by wetting said body with a spermicide and inserting said body intravaginally to act as a barrier to the os uteri and to fill the fornices of the upper vault of the vagina, including the steps of storing said body in a container adjacent the stored body of said spermicide and releasing said spermicide upon command to moisten said body prior to intravaginal insertion, wherein the body is shaped during compression from two discs of said material into a pair of folded umbrella configurations, wherein the apexes face in opposite directions, with the discs being joined at their centers, and inserting said compressed folded umbrella configuration into said container.

3. As a new use for a known material, the method of using a body of purposefully compressed, compression self-retentive, hydrophilic, fluid expansible material having a high coefficient of expansion and the capability of becoming resilient upon wetting as a barrier contraceptive by wetting said body with a spermicide and inserting said body intravaginally to act as a barrier to the os uteri and to fill the fornices of the upper vault of the vagina, including the steps of storing said body in a container adjacent the stored body of said spermicide and releasing said spermicide upon command to moisten said body prior to intravaginal insertion, wherein the body is shaped during compression from two discs of said material into a pair of folded umbrella configurations, wherein the apexes of the umbrella face in opposite directions, with the discs being joined at points on their peripheral edges, and inserting said compressed folded umbrella configuration into said container.

4. The method as set forth in claim 2, further including the step of folding said material, and inserting said folded material into said container for edgewise expulsion intravaginally.

5. The method as set forth in claim 4 wherein the shape of the body is selected from any one of the following shapes:

an irregular pentagon; a squared circle; a rectangle with rounded corners; and a circular disc.

6. The method as set forth in claims 1 or 2 wherein the discs are stitched at their centers to minimize rotation thereof.

7. The method as set forth in claims 1 or 2 wherein the perimeters of said discs are notched.

* * * * *